United States Patent [19]

Sjogren

[11] Patent Number: 4,971,796
[45] Date of Patent: Nov. 20, 1990

[54] SLOW RELEASE PEST CONTROL GRANULE COMPOSITION

[76] Inventor: Robert D. Sjogren, 14 Black Oak Rd., St. Paul, Minn. 55127

[21] Appl. No.: 254,283

[22] Filed: Oct. 5, 1988

[51] Int. Cl.$^5$ ............................................. A01N 25/26
[52] U.S. Cl. ....................................... 424/417; 424/80; 424/408; 424/409
[58] Field of Search .................. 424/417, 409, 408, 21, 424/80

[56] References Cited

U.S. PATENT DOCUMENTS

| | | | |
|---|---|---|---|
| 4,007,258 | 2/1977 | Cohen et al. | 424/80 |
| 4,341,759 | 7/1982 | Bogentoft et al. | 424/417 |
| 4,732,762 | 3/1988 | Sjogren | 424/408 |

FOREIGN PATENT DOCUMENTS

| | | |
|---|---|---|
| 77038097 | 3/1974 | Japan . |
| 58062102 | 10/1981 | Japan . |
| 59020209 | 7/1982 | Japan . |
| 59139306 | 1/1983 | Japan . |
| 59181201 | 3/1983 | Japan . |
| 60097901 | 11/1983 | Japan . |
| 59-001682 | 1/1984 | Japan . |
| 60-237007 | 11/1985 | Japan . |

Primary Examiner—Merrell C. Cashion, Jr.
Assistant Examiner—P. L. Prater
Attorney, Agent, or Firm—Merchant, Gould, Smith, Edell, Welter & Schmidt

[57] ABSTRACT

A layered pest control agent comprising layers of a proteinatious material, and an intermediate spacing layer between the proteinatious layers where more than one proteinatious layer is used, can release pesticide into the environment at a controlled rate sufficient to control a pest population during a breeding season.

69 Claims, No Drawings

SLOW RELEASE PEST CONTROL GRANULE COMPOSITION

FIELD OF THE INVENTION

The invention relates to a pest control composition and to a solid pest control means made from the composition that can be distributed evenly throughout an area to slowly release an effective pest controlling amount of a pesticide for a prolonged period to control pest populations during temperate months or during a pest breeding season or during a particular portion of a reproductive cycle. The invention also relates to methods for pest control using the pest control means.

BACKGROUND OF THE INVENTION

During the temperate months of the year many pest populations in various areas of the U.S. reach levels causing severe problems. One pest, the mosquito, can be distracting, can cause bites which itch, and in certain areas can be a vector for the spread of communicable disease such as equine encephalitis. Mosquito populations vary during temperate periods of the year, depending on rainfall, temperature, and other conditions. While the lifespan of an adult mosquito is not long, mosquito larvae can continually mature throughout the year into the adult stage, resulting in the continuing resupply of the mosquito population. Many communities have combatted mosquito populations by fogging or spraying the environment with an insecticide, adding insecticide to likely hatching sites, and by distributing a variety of slow release insecticide compositions into the environment.

The treatment of large areas of the environment having significant numbers of trees, shrubs, and other vegetation requires a particular form of pest control agent to effectively control populations. A pest control agent in the form of dense granules is preferred in aerial applications. Such dense granules permit applications of pest control agents in winds up to 14 miles per hour as these granules can penetrate dense vegetation canopies present during the summer months. Dense granular pest control means can remain effective for extended periods of time when applied to field sites in advance of breeding. During the breeding season dense granules can regulate the rate of pesticide release over an extended period of time.

In one embodiment, the pest control means can be applied to a site, can be activated by flooding, and while wet, release significant proportions of the pesticide.

Many other pests can cause severe problems during their growth or reproductive cycles. Such cycles generally correspond to the temperate seasons of the year. Mollusks in both the adult and larval forms can infest fresh water, damage flora and fauna, provide a disease vector, and pose cosmetic problems. Fungi and algae grow rapidly in fresh water and can make water unpleasant for recreational purposes, may produce toxins which poison farm animals and may make water unfit for human consumption. A variety of plants can grow in unwanted areas, reducing crop yields and presenting weed control problems in many residential and agricultural environments.

Many attempts have been made to combat these pest control problems using a variety of pesticides. Pesticides have been encapsulated with both macro and micro-encapsulation processes, in ceramic materials, biodegradable polymers, porous mineral supports, cellulosic derivatives, polyurea compounds, gypsum and other supports in order to protect the insecticide from the environment and to ensure a controlled release, attempting substantial control of pest populations. An effective pest control concentration is defined as a concentration effective to kill a substantial fraction of at least one form or stage of the pest during its life cycle, or a concentration effective to prevent development or maturation of a form or stage of the pest during its life cycle. The pesticide should be released by the pest control means at an even rate such that significant amounts are not wasted. Pesticides should be protected from the effects of atmospheric oxidation, electromagnetic radiation (light energy or ultraviolet radiation), or other factors, which cause the chemical decomposition of the pesticide. In areas of dense vegetation the pest control means can be of small size, 0.5 to 4.0 mm in diameter, to permit even distribution and penetration of such dense vegetation in environmental areas where pest control applications are needed, and of a distribution density which is at least about $5.5\times10^{-5}$ $gm/cm^2$ to provide for adequate distribution over the desired areas when applied by fixed wing and rotocraft. The pesticide composition and means should comprise natural materials, be biodegradable, and be of low cost.

Accordingly, a substantial need exists for a controlled release granule pest control composition that can be made into a granular pest control means and can be applied by aircraft or by hand. A further need exists for a pest control means that can provide substantial control of pest populations for a period of 10–30 days, which protects the pesticide from substantial degradation, effectively penetrate dense vegetation, provide multiple and uniform placement of controlling particles throughout the treated environment, and provide a controlled, continuous rate of release that maintains an effective pest controlling concentration of pesticide in the environment.

BRIEF DISCUSSION OF THE INVENTION

I have found a composition comprising a pesticide in the form of slow release particulate comprising as a core, an inert or active particle, and at least one layer of proteinatious material, and when layers of a proteinaceous material are used, a separating layer. I have found that the pesticide can be used in the core, the proteinaceous layer or in the separating layer or both to control the target pest. Proteinaceous material can be crosslinked by typical crosslinking agents including aldehydes, dialdehydes, di or trivalent metal ions, and others. The pest control agents can additionally comprise materials that protect the pesticide from chemical degradation caused by environmental factors or that regulate release.

The novel slow release pest control composition is used in the environment by distributing a composition comprising a particulate core with coatings comprising proteinaceous materials and intervening separating layers. The proteinaceous and separating layers can contain the pesticide. Uniform or controlled dissolution of the coated protein or separating films releases the pesticide at controlled rates into the environment. For reasons of ease of manufacture and controlled distribution of the pest control means, the means takes the form of regular, generally spherical, uniform particles. The proteinaceous material surface of the particle can slowly dissolve throughout the temperate or pest breeding season until the coating is substantially gone. The pesticide provides a continual smooth release of the control agent at a constant or at a rate that does not waste excessive amounts of pesticide at an effective concentration of pesticide.

The proteinaceous material used in the releasing layers of the invention are prepared with varying degrees of thickness or insolubility resulting from crosslinking. The rate of decomposition or dissolution of the proteinaceous material is dependent both on the degree of crosslinking as well as the thickness of the proteinaceous material. The decomposition or dissolution of the proteinaceous material is most effective when the pest control means is fully immersed in free water. However interstitial water present in soils can similarly cause the dissolution or decomposition of the proteinaceous material resulting in pesticide release.

The term pest is intended to cover any living organism, plant, animal or microbe, whose presence causes human discomfort, harm to agriculture, a health hazard, or cosmetic harm. The term pesticide means any chemical agent effective in pest control, that operates to control pest populations which prevents maturation or reproduction of any stage of the pest, or which kills any stage of the pest with toxic effects.

DETAILED DISCUSSION OF THE INVENTION

In accordance with the present invention, there is provided a controlled slow release pesticide composition comprising an active or inert core, a pesticide, at least one collagen protein compositional layers, and when more than one protein layer is used, an intervening separation layer between the protein layers. Optionally, the controlled slow released pesticide composition of the present invention may carry a drying agent on its outer surface.

Core

The core of the controlled slow released pesticide composition of the present invention can be active or inactive and can serve a variety of functions depending upon the intended end use of the composition. For instance, an inert or solid core may be desired to provide added weight to the pesticide composition of the invention. Added weight in the individual particles or granules of the pesticide composition may be beneficial if the particles are to be applied over the intended area from the air by helicopter or airplane. In contrast, if the slow released pesticide composition of the present invention is to be applied by hand, a solid particle having less relative mass may be desirable for use in the controlled slow release pesticide of the present invention.

Another consideration which affects the choice of materials used for the core is the available surface area required of the core particle. Specifically, the core must have adequate surface area to allow coating of the alternating proteinaceous and spacing layers as will be discussed further herein.

Generally, given the considerations of mass and surface area, the core may be anything that has a certain internal or surface particle size. The desirable particulate core has a diameter ranging from about 1 mm to 4 mm. Specific types of materials which may be used are sand, vermiculite, diatomaceous earth, clay, or particulate cellulosic or organic type substances such as ground peanut hulls. Another source of core material is corn cob particles known as Grit-0-Cobs TM available from The Andersons Corporation in Maumee, Ohio.

As an alternative to a solid or granular core, a porous core may be used when dealing with active chemicals which are either insoluble, or difficult to combine with the proteinatious or spacing layers. In such an instance, the active chemical will be solubilized within a carrier solvent. The carrier solvent will be vacuum loaded into the porous core element where upon the solvent will be allowed to evaporate. The solid core is now loaded with the active chemical and ready to be further coated with the proteinatious and spacing layers. By varying the extent of the subsequent protein coating, the time interval can be varied as to when the active chemical is released. Varying the degree of proteinatious coating amongst a large quantity of pest control means allows a continued secession of pesticide release at varying intervals over a given time period.

Generally, any porous core will allow the vacuum loading of an active chemical. Core materials which can be used, for example, are those absorbent or porous cores which were mentioned above, specifically, particulate cellulose such as ground peanut hulls , diatomaceous earth, activated charcoal, bubbled amorphous silicate commercially available from Grefco Corporation as DICAPERL ®, porous polymeric material such as polyethylene, polypropylene, polyethylene oxide, and ethylene/acrylic acid salt copolymers commercially available from Akzo Chemical can be used as porous core materials.

Alternatively, when the intended application requires a higher concentration of active, the core may comprise the specific pesticide to be used. In such an instance, the pesticide is not intermixed with the proteinatious or carbon layers, but instead, is overcoated with these secondary layers. In this instance, the proteinatious and spacing layers will be scaled by thickness as well as protein cross-linking to define a pesticide granular particle which releases the entire load of active at one time. The controlled slow release effect is, in turn, provided by formulating particles having varying degrees of coating crosslinking and thickness and which, in turn, will release the active pesticide at various time intervals. Particles having release effects after time intervals of different length are then intermixed to provide a pesticide composition having a continued controlled slow release effect after application to the intended environment of use.

Pesticide

The term pesticide as employed here is intended to include any active material used for control of unwanted plants, insects, animals, or microorganisms, such as mosquitoes, fungi, algae, snails, weeds, including in particular insecticides, herbicides, biocides, and other control or management materials utilizable in the environment.

A great variety of pesticides can be used which are compatible with the technical protein colloid and carbon particle components of the invention. Representative of the pesticides which may be employed as starting materials in the invention are those disclosed in U.S. Pat. No. 4,225,693, which are expressly incorporated herein by reference. In general, exemplary pesticides compositions include triazole insecticides, arsenic based insecticides, sulfonyl carbamate insecticides, thiazine insecticides, benzonitrile insecticides, which are set forth in column 3, lines 21-70, columns 4, 5 and 6, lines 1-10, organophosphate, and pyrethroid insecticides. No list of useful pesticide can be complete since there are pesticide of which I am not aware of and new pesticide useful in this invention will be developed in the future. However, any pesticide having insect control properties which can be compatible with technical protein colloid and carbon can be used in the invention.

The pesticides which are preferred for use in the invention are trichloroacetic acid, 2,4-dichlorophenoxyacetic acid and 2,4-DW, a relatively new pesticide 4-amino-6-tertiary butyl-3-(methythio)-AS-triazine-5(4HN)-one, which is available under the name Metabucin. The most preferred mosquito insecticide comprises isopropyl-(2E,4E)-11-methoxy-3,7,11-trimethyl2,4-dodecadienoate, which is the active ingredient in the composition, available under the trade name Altosid Liquid Larvicide from Zoecon Corporation. Altosid Liquid Larvicide is an insect specific growth regulator that acts to prevent the emergence of adult mosquitoes from the pupae stage by affecting only the maturation process and is not a nondiscriminant toxin.

Many fungi can be controlled using the pest control means of this invention in a variety of environments, including agricultural and industrial applications. In agricultural applications fungi can often harm the maturation of agricultural plants or animals, resulting in the loss of valuable commodities. In industrial applications, fungi often grow in places where water accumulates such as cooling towers, streams, tanks, filtration mechanisms, etc., causing plugging, odor problems, etc.

Fungal control agents which can be used in the pest control means of the invention include sulfur, polysulfides, heavy metal fungicides, such as copper based, arsenic based, and mercury based fungicides, including for example copper hydroxide, copper carbonate, cuprous oxide, O-(chloromercury)phenol, cresyl-mercuric cyanide, methylmercuric-8-hydroxy quinolate, phenyl mercuric acetate, and phenyl N-(ethylmercury)-paratoluene sulfonamide; organic fungicides such as quinones, chlorinel, dichlone, and others. Organic sulfur based fungicides include ferric dimethyl dithiocarbamate, zinc dimethyl dithiocarbamate, and sodium methyl dithiocarbamate; and other classes of organic fungicides including imidazoline based fungicides, quinoline based fungicides, trichloromethyl thiodicarboxamide based fungicides, and others.

Molluscicides can be incorporated into the pest control composition of the invention. Mollusks are invertebrates which comprise snails, slugs, oysters, mussels, cuttle fish, squid, and other animals. Mollusks can attack crops, flower gardens, and infest fresh water and can be the vector for a variety of disease causing parasites. Molluscicides useful in the invention include metaldehyde, antimony based molluscicides, and carbamate based molluscicides such as isolayn or sectraon. Molluscicides that can be used include copper sulfate, niclosamide, copper dimethyl dithiocarbamate, dinitrol phenol based molluscicides such as 2,4-dinitro creosol and any other molluscicide that can be incorporated without adverse effect into the composition of the invention.

Herbicides that can be used to effectively control unwanted plants in residential or agricultural environments are well known chemical herbicides that kill growing plants or prevent seed germination of plant growth. Most useful herbicides belong to compound classes including the phenoxy alkanoic acid such as 2,4-D, 2,4,5-T, 2,4-DD, MCPA; the S-triazines, cymazines, detrazine, propyzene; the phenyl carbamates, IPC, CIPC, barban; the chlorinated aliphatic acids, delapon, TCA; the phenylureas (fenuron, monuron, diuron); the dinitrobinzenes (DNBP, trifluralin, benefin); the benzoic acids, dichlobenil, amiben, 2,3,6-TBA; the dipyridyls (paraquot, diquot); and the dithiocarbamates, EPTC, and vernolate.

Algecides can also be incorporated into the slow release pest control means of the invention. A variety of both organic and aeroganic algecides are well known in the art.

Protein Constituent

The proteinatious layer can be made of any protein composition that can be used in aqueous solutions or suspensions.

Preferred colloid proteins are high molecular weight, long chain, organic colloids of complex protein structure. They are obtained from a variety of natural proteinatious sources. The most common source is collagen, the principal intercellular constituent of connective tissues. Such proteins consist of chains of amino acids bound to each other through their amino and carboxyl groups, and upon digestion yield various amino acids joined in polypeptide linkages to form linear polymers in definite ratio.

As hydrophilic colloids they are typically soluble in water or polyhydric alcohols provided water is present. Placed in cold water they swell to a soft spongy mass, imbibing water. Upon heating, the hydrated mass readily melts into solution in the temperature range of 100° to 115° F., the result is a macromolecular dispersion. Solutions gel upon cooling below their melting points, gradually set to strong elastic gels, and when dry, form hard, lacquertype finishes. As reversible colloids, they dissolve over time when placed in water in proportion to degree of insolubilization and water temperature.

Typically on a molecular level the protein colloid molecules are long helical in shape and distinctive in forming insoluble fibers that have a high tensile strength. Immature collagen from the tissues of young animals can be extracted because of the absence of covalent cross links, making it feasible to extract the basic structural unit tropocollagen. Tropocollagen has a rod shape 3,000 A long and 15 A in diameter, which form as three helical strands which wind around each other to form a strong cable. The structural design of the collagen fiber is a quarter-staggered array of tropocollagen molecules. Heating tropocollagen results in great change in the physical properties, in which the viscosity of the solution drops sharply indicating that the molecules have lost their rodlike shape. Thus thermal motion overcomes the forces that stabilize the triple-stranded helix, yielding a disrupted structure which is a random coil.

The technical protein colloid powder, when mixed well with water, will require about equal parts of water to that of collagen to hydrate. Once the colloid has swollen, heating to 130° F. will give a workable heavy viscous solution which can be diluted further with warm water. Collagen is compatible with a variety of water soluble natural and synthetic polymers, such as casein, carboxymethyl cellulose, methylcellulose, sodium alginate, starch and other additives which can provide properties such as wettability, strength, hardening rate and viscosity.

Preferred collagen compositions having a controlled rate of release, disintegration or deterioration in the environment comprise collagen insolubilized to a controlled rate of dissolution over time. These collagens can slowly dissolve over a time period of 10 to 30 days slowly releasing the pesticides into the environment during the decomposition period.

The most preferred collagen for making the improved slow release mosquito control compositions of this invention comprise a high molecular weight, high purity colloid having a molecular weight of 10,000 to 80,000 and at least a 20% percent by weight solution. Preferably the colloid will have a molecular weight of 15,000 to 60,000 and at least 30 percent by weight solution, and even more preferably a molecular weight of about 20,000 to 40,000 and at least 35 percent by weight solution and greater. These ranges are preferred for reasons of slow decomposition in the environment resulting in the extended lifetime of the composition and the active concentration of the pest controlling agent throughout the desired control period.

Crosslinking Agent

In order to reduce the solubility of the proteinatious layer of the present invention two mechanisms may be used. First, the proteinatious layer may be deposited in a thicker layer or, alternatively, the technical protein may be crosslinked prior to application. The crosslinking agents useful in the present invention function to bond the amino and carboxy groups in the technical protein colloid thereby reducing the aqueous solubility of this layer. Generally, any agent which will provide the desired effect of crosslinking the technical protein colloid may be used in the present invention. Specifically, aldehyde crosslinking agents as well as trivalent metal ion crosslinking agents have been found to provide a high degree of utility in crosslinking proteins used in the composition of the present invention.

While we do not wish to be held to a theory of action of the pest control means of this application, we believe that the controlled rate of film dissolution and hence the active ingredient release can be a result of either the molecular weight of the protein or extent of the crosslinkage of the protein molecule or both. The progressive increase of crosslinking renders the protein increasingly less soluble with an increasing extent of crosslinkage between the protein molecules which in turn controls the release of the pesticide. The molecules in the colloid appear to overlap and interlink with the addition of aldehyde, resulting in a high strength film having strength and a controlled rate of solubility resulting from the crosslinked structure. These properties appear to provide the controlled solubility and controlled release of the pesticide compositions.

Water soluble proteins react with aldehydes to increase apparent molecular weight and reduce water solubility. This apparent increase in molecular weight and concomitant decrease in solubility of the colloid protein results from the promotion of what is commonly referred to as "cross-linking" in the colloid composition. The aldehyde cross-linking of colloids is principally affected by the reaction of an aldehyde with the amino group of the colloid. The formation of hydrolizable cross-links in proteins is thought to take place over several steps including the formation of a methylol or substitute methylol derivative, and possibly substitution of the amino group for a hydroxyl which results in the crosslink bond. Aldehydes commonly used to crosslink proteins include formaldehyde and gluteraldehyde. It is thought that formaldehyde follows a reaction pathway which includes the formation of a methylol derivative and a resulting, unstable, hydrolizable crosslink collagen. In contrast, gluteraldehyde irreversibly cross-links collagen through a reaction pathway which includes the amine to aldehyde addition reaction, a subsequent aldehyde condensation reaction, and at some point an oxidation step.

The presence of urea in solution can retard the cross-linking reaction and for these reasons can be necessary in manufacturing processes. The addition of aldehydes such as formaldehyde, or Glyoxal in amounts of 0.1% to 5% by weight to collagen solutions can significantly, and proportionately, reduce the water solubility of subsequently dried collagen and hence be used to regulate the dissolution rate of colloids containing pesticides in finished formulations. Preferably, the aldehyde concentration used can range from about 0.2 wt-% to 2 wt-%, and most preferably 0.25 to 1 wt-%. As the crosslinking rates become higher, the protein can become more highly insoluble and can become similar to brittle leather. Finally, the quantity of such protein colloids used in preparing controlled release formulations is also directly related to the duration of release over time, and can be used as a variable to regulate release.

Proteins may also be cross-linked by the use of basic bivalent and trivalent ionic species such as trivalent chromium sulfate. Briefly, the cross-linking process follows a pathway which culminates in the formation of a bidentate sulfate bridge through the replacement of the $SO_4=$ion with $H_2O$ in the chromium sulfate molecule. The eventual substitution of $H_2O$ with $OH^-$ condensation produces an olate bridged binuclear structure with monodentate sulfate groups. For greater detail on either aldehyde or valence metal ion cross-linking see Friedman, M. *Protein Crosslinking, Biochemical and Molecular Aspects*, (Ch. 27, pages 425–440; Plenum Press 1977) which is incorporated herein by reference.

The technical protein colloid is prepared for use by hydrating dry colloid crystals or powder in cold water to allow them to swell completely. Once the colloid is hydrated it is slowly heated, with stirring, to a temperature of 120° to 130° F., but not to temperatures above 140° F. When the protein colloid is heated to the appropriate temperature, the microencapsulated insecticide is then added to the colloid, and the combined solution is again heated to a temperature of 120° F. prior to spraying. When the pesticide is not microencapsulated, but rather the technical pesticide is a fine crystalline powder, a protein colloid base is sprayed on the sand particles and a portion of the total amount of technical powder is added to the coated sand particles which then causes it to attach to the particles. A second spraying of colloid is added to the granules, followed by more technical powder, and a third application of colloid and technical powder.

When all technical insecticide powder has been added, a final colloid spraying is added, and finally a drying powder can be added and tacked onto the outside of the granule. While the outer coating of powder is not essential to the invention, the application of a drying powder is preferred to prevent the granules from sticking together and finalize processing. A coating of a powder such as, for example, carbon which will adsorb and desorb the pesticide as well as functioning as a sunscreen. Any other sorbtive dust can be used which will adequately fulfill the drying function. In selecting a sorbtive dust the specific characteristics which must be focused on are the available pore space of the dust which, in turn, determines the absorbency and drying capability of the dust. Along with carbon, representative examples of sorbtive dust which can be used as drying agents are diatomaceous earth available from Eagle Picher as MN-47 Diatomite, and activated silica available from Johns Manville as Hysil.

If the technical insecticide is an oily liquid not compatible with the protein colloid solution, the insecticide may be dissolved in a solvent such as 1,1,1-trichloroethane which is then evenly sprayed on an activated charcoal powder such as Norit SG, and the solvent evaporated. This powder is then attached to the sand particle by alternating applications of protein colloid and insecticide treated charcoal powder, in the same manner as in the case of insecticide technical powder.

If the active ingredient, whether pesticide, herbicide, insecticide, etc., is a solid having a high solubility as well as a high vapor pressure, particles of the solid active ingredient are coated through the use of a fluid bed dryer, granulator, or coater. In such a case, the coating chamber of the fluid bed coater is charged with the particles or spheres. The fluid bed coater is then activated suspending the particles within the chamber. The particles may then be sprayed from any variety of angles or openings provided in the chamber wall.

The advantage to using such technology is that the particles retain a regular coating of uniform thickness of the proteinatious and intermediate compositions. Moreover, once fully coated, the particles are dried while suspended in the machine. This automatic drying precludes the tacking together of the particles when the machine is tacking together of the particles when the machine is deactivated and the particles are removed. Fluid bed dryers, granulators, and coaters are available from companies such as Aromatic Inc. and Glatt Air Techniques Inc. One example of a fluid bed coater which can be used to formulate the composition of the present invention is the Glatt Powder Coater Granulator (GPCG). The GPCG is a twin chamber unit having a processing chamber and a storage chamber. Once the machine is charged with the core particles, the particles are coated and dried. The particles are then transferred to a separate storage chamber through air pressure.

The pest control means must be formulated with the correct total amount of active ingredient to release and maintain the minimal effective dose rate per day, to achieve complete pest control during the period of time of which the granule is designed. The formulation must provide an accurate incremental release of active ingredient each day to release only that amount of insecticide necessary to achieve control, yet protect the remaining active ingredient from degradation until actually released. The formulation release rate must be adjusted to reach the concentration needed to achieve control within 48 to 72 hours, and thereafter release only that rate which will offset the daily rate of degradation of the active ingredient in the site from environmental factors.

The rate of pesticide release over time in this invention is controlled, in part, by certain factors. Among these factors are the molecular weight of the protein collagen, the degree of crosslinkage of the protein helix with aldehydes or trivalent metal ions, the use of other insolubilizing agents, and the quantity of collagen used in the formulation. Technical protein colloid polymers exist with a range of molecular weights from approximately 10,000 to 120,000, most commonly with molecular weights of 20,000 to 80,000. Lower molecular weight colloids are more water soluble than high molecular weight colloids.

Spacing Layer

Intermediate of the inner and outer proteinatious layers of the composition of the present invention is a spacing layer. This intermediate spacing layer functions as an additional medium for carrying the pesticide compositions used in the invention as well as by providing physical characteristics which optimize the controlled release of the pesticide, adjustment of the specific gravity of the individual granules, and protection of the pesticide against degradation by solar or electromagnetic energy.

Generally, the composition of the spacing layer will depend on whether the layer is intended to be loaded or carry the active pesticide of the present invention. In such instances, the spacing layer should comprise an absorbent powder similar to the sorbtive dust used as drying agents. Here again, substances such as particulate carbon, diatomaceous earth available from Eagle Picher as MN-47, and activated silica available from Johns Manville as Hysil will adequately serve as a spacing layer. Moreover, the spacing layer may be the insecticide or pesticide itself if they exist in a powdered form.

Alternatively, if the spacing layer is to be principally inert or unloaded with insecticide, any substance which will function to dry and extend the surface area and, in turn, the area in which the proteinatious layer containing the active pesticide can be deposited on will work as a spacing layer. Preferably, activated charcoal or carbon particles are used for the spacing layer as this composition affords and optimal chemical and physical properties to the spacing layer.

Finely divided carbon compositions useful in the invention for making the delayed release mosquito control composition of the invention are carbon compositions having large surface area and small particle size, providing the electromagnetic radiation protection and the release smoothing properties. As the pest control means comprising the slow release composition decomposes, the mosquito controlling agent is released. The carbon in the composition tends to smooth the release rate by absorbing extra concentrations of insecticide when the release rate is high and by releasing or desorbing the insecticide when the release rate is low.

The carbon particles in combination with the nonencapsulated, encapsulated, or micro-encapsulated pesticide also appear to control the release locus of the pesticide. For instance, objects with a specific gravity substantially less than 1.0 tend to float while those with a greater specific gravity tend to sink. Pesticide compositions can have a specific gravity substantially less than 1.0 which results in the pesticide floating to the surface where it can be rapidly degraded by contact with light and air. The pesticides in combination with carbon can be made to have a specific gravity greater than 1 which results in the carbon-pesticide means that can maintain a neutral buoyancy at a constant depth or can sink to the bottom for release. The ability to adjust the specific gravity of the carbon-pesticide means is of particular value where the active pesticide has a low water solubility and a specific gravity of greater than 1.0. Use of a carrier having a specific gravity of less than 1.0 assists in distributing the pesticide by the particles rising and being distributed within the intended area of application. Otherwise, the pesticide may merely pool below the pellet as it dissolves. By adjusting the specific gravity of the technical protein colloid pesticide particle combination the speed with which the pesticide reaches the surface of the body of water can be closely controlled. The carbon particles also protect the insecticide by absorbing electromagnetic radiation and preventing the deterioration of the insecticide through the effects of such radiation.

Accordingly, preferred particulate carbon useful in the invention has a large surface area and a small particle size found in carbon sources such as activated carbon, finely divided charcoal, etc. Further details of sources of finely divided carbon are found in *Kirk-Othmer Encyclopedia of Chemical Technology*, 2nd Edition, Vol. IV, pp. 149-335.

Alternatively, other buoyant constituents may be used to assist in the dispersion of pesticides having a low solubility. For instance, cellulosic materials such as Grit-O-Cobs TM or RGP Corn Cob products, available from The Andersons Corporation in Maumee, Ohio may be used to carry the active ingredient. In such a case, the pesticide is solubilized in a solvent and sprayed onto the particles. After the solvent has evaporated, the buoyant cellulosic particle is then wholly incorporated into the proteinatious layer of the slow release pest control means. After the slow release pest control means is placed in the intended environment of use, the cellulosic corn cob particles loaded with pesticide will be released upon dissolution of the proteinatious layer and in turn be dispersed to the surface where the pesticide will weep from the particles. Other material which may be used for this function of the invention include bubbled amorphous silica available from Grefco, Inc. as DICAPERL TM and microporous polyolefin beads available from Enka, a division of Axzo Corporation, as ACCUREL TM. It should be noted that these buoyant ingredients, once ladden with active pesticide, may be intermixed with either the proteinatious layer or the spacing layer. Consequently, the present invention offers a broad range of designs to satisfy any number of intended applications requiring active ingredients and pesticides which are often very difficult to use and disperse.

In somewhat greater detail, the slow release pest control means is formed from an effective amount of a pesticide; sufficient technical protein colloid to result in a slow dissolution of protein colloid lasting for the duration of control of immature mosquitoes or other pest species (commonly 10 to 40 days, preferably); sufficient amount of charcoal to prevent decomposition of the insecticide, and to smooth the release of the insecticide; sufficient water to be workable in manufacture, and a clean particulate base.

The slow release pest control means can take the form of a particulate pest control having a coating of any arbitrary shape of regular or irregular thickness on the surface of the particulate. To a great extent the shape of the means can result from the shape of the particulate and the loading of the pest control composition. The pest control means can approximate the shape of the particulate, particularly at low loadings. Depending upon application mode the pest control composition can have any arbitrary shape. However, if the pest control composition is sprayed on a particulate, the pest control means becomes roughly spherical. The release rate of the pest control agent from the means appears to be proportional to the means surface area and solubility. The surface area should range from $1mm^2$ to about $20mm^2$, preferably $1mm^2$ to $2mm^2$, and most preferably $2mm^2$ to $3mm^2$, depending on the concentration of the pesticide to the means and total amount of control agent desired to be applied per unit area in field treatments. The preferred form of the slow release composition is in the form of a sand core granule having grain dimensions of about 2mm to 4mm diameter or radius. Surface coatings on larger cubes, cones, etc. of solid body containing active ingredients can control the release of the inner body.

The most preferred form of the slow release composition is in the form of a 10 to 25 mesh round coated granule or active ingredient particulate. I have discovered that in methods for manufacturing the slow release pest control object that the liquid colloid addition and the addition of pesticide powder or charcoal powder must be carefully managed to prevent the granules from forming large balls.

The preferred method of coating the particulate is to alternate spraying of the technical protein colloid on the dry particulate surface with the addition of powders while tumbling or blending all dry ingredients in a rotary mixer or ribbon blender. For ease of application and to achieve the most uniform application of the active ingredient, and balanced release of the slow release compositions, the granules should be uniformly coated with alternating layers, layers of an evenly dispersed fluid mixture of technical protein colloid and pesticide, alternate with layers of carbon powder. The attachment of the carbon powder to the damp surface of the coated granule serves to dry the coated surface and thus prepare it to receive the next layer of liquid spraying. A cool particulate surface speeds the gellation process of the protein colloid and hence favors a uniform granule formation.

The slow release pest control composition can comprise from about 5 to 30% technical protein colloid, preferably about 10 to 20%, and most preferably 15 to 25% protein colloid, depending on the length of controlled release desired. The slow release composition of the present invention can comprise as much as about 80 wt-% to 90 wt-% active ingredient if the active is the particulate core of the composition. Otherwise the slow release composition can comprise 40 wt-% or less of an active ingredient agent if the active is carried in the protein or spacing layers, preferably 30% or less of controlling active ingredient, and most preferably, for reasons of economy, ease of handling, and effective pest control the composition can contain about 1 to 20 wt-%, preferably 2 to 15 wt-%, most preferably for reasons of efficient mosquito control for a prolonged duration 5 to 25 wt-% of the pest control agent. Alternately the amount of pesticide will be less than about 40 wt-%, preferably less than about 30 wt-%, most preferably about 5 to 25 wt-%. The composition can comprise less than about 10 wt-%, preferably less than about 8 wt-%, most preferably about 4 to 6 wt-% of charcoal or activated carbon in order to protect the insecticide and to control the release of the insecticide composition. Sufficient water (about 60 to 80 wt-%) is added to the mixture of technical protein colloid to hydrate the colloid allowing it to swell. The addition of heat to temperatures of 120° to 130° F. reduces the viscosity of the solution and permits spraying.

In general, the pest control means can be applied to a field site at a rate of about 3 to 20 lbs. of granules per acre, most preferably 5 to 7.5 lbs. per acre. Commonly the spacing of pest control means in the breeding site is 2 to 12 granules per square foot, most preferably 4 to 8 granules per square foot. The even distribution of granules provided for by the large number of particles per pound is of particular advantage in controlling pests through likely breeding territories where the topography is substantially unknown. Pest control means formulated on sand granules of high density per cubic foot are of particular value to achieve penetration of control means where dense vegetation canopy or thatch hinders achieving effective penetration and control. Where pests develop in many small depressions or hoof print type pockets, the use of control means in the form of many particles which can be placed in each pocket is necessary to achieve effective control.

The pest control means is particularly valuable as it permits applications to known important pest breeding locations which contain eggs, larvae, seeds, spores, etc. when such sites are dry at the time of treatment. Such prehatch treatments are of significant operational and economic benefit, as they allow historically important pest breeding sites to be treated prior to rainfall or irrigation. This allows the time after rainfall (which is normally the only time control measures can be applied to larvae in the water), to be used to achieve control over additional breeding sites, which otherwise could not be treated. The pest control means can be distributed into the environment by hand, can be distributed from ground vehicles, or boats, can be distributed by helicopter or other aircraft, or any other means ensuring a fairly even distribution of the pest control means into the environment.

The pest control means of the invention can be distributed into any environmental location which is seasonally moistened by rainfall, flooded or contains standing water during a substantial portion of the season. Typical wetland areas which can be treated using the pest control means of the invention are seasonally flooded basin or flat sites typical of woodland areas having aquatic plants or grasses. Such sites generally are flooded during the wetter periods of the temperate season. Inland fresh meadow areas contain standing water for greater periods of time during the year and are commonly characterized by the presence of reeds, canary grass or other plants common in a water environment. Inland shallow fresh water marshes are commonly muddy throughout the growing season with about 6 inches of water, commonly characterized by the presence of cattail ranks, and grass across geographically depressed areas. Inland deep water, fresh water marshes, commonly have water year around, pockets of open water permitting submerged aquatic plants to grow, and can have as much as six inches to three feet of water permanently present. Inland open fresh water such as game lakes commonly have fresh water present at depths of greater than 10 feet, and can be characterized by depths free of vegetation while vegetation is commonly present in the shallows or at the water edge. The pest control means can be used in any of these wetland areas in order to control pest populations.

Mosquitoes, for example, are most commonly produced in areas that are seasonally flooded or where the water depth fluctuates. The pest control means can be applied to an environment that is substantially dry or wet. In a dry environment (no standing water) atmospheric humidity will result in little pesticide release. In wet environments (standing water) where the pest control means is immersed, water that induces decomposition will generally be environmental standing water. It is to be understood that decomposition is generally favored and is most efficient in the presence of intermittent standing water, or interstitial water in soils.

EXAMPLE I

Into a 10 gallon stainless steel tank, with heating jacket adjusted to maintain 130° F., was placed 2 gallons of 130° F. water. A high speed shear mixer, such as used in paint manufacturing, was inserted into the water and adjusted to 800 to 1,000 rpm. Next, 7.7 pounds of dry powdered collagen protein (Technical Protein Colloid # 1 V, Swift Adhesives and Coatings, Chicago, Illinois) was slowly added into the vortex of the water and mixed for 2 minutes to dissolve the powder. The high speed blade was then removed and a slow speed paddle blade inserted and adjusted to 30 to 50 rpm. Then 5 gallons of a slurry of micro particulate encapsulated mosquito control agent isopropyl(2E,4E)-11-methoxy-3,7,11-trimethyl-2,4-dodecadenoate (Altosid Liquid Larvicide, Zoecon Industries, Dallas, Texas) 5–10 micron particles, 5% slurry s-methoprene of micro encapsulated particles in water, 0.86 lb./gal. (103 gm/1) was added and mixed while the fluid mixture was heated to a temperature of 130° F.

While the technical protein colloid and pesticide slurry was heating, a ribbon blender of 3 cubic yard capacity was charged with 950 pounds of washed # 30 Red Flint Filter Sand (American Materials, Eau Claire, Wisconsin). While mixing at low speed in a pressure vessel with heating jacket, the vessel was pressurized with air to 40 psi. The ribbon blender was started and the solution sprayed through a flat fan nozzle system (Spraying Systems #8001 nozzles) affixed inside the ribbon blender, and adjusted to spray onto the rotating sand. When the sand changed from free flowing to the point at which it began to drag heavily after the spraying of approximately 3.5 gallons, and before it began clumping, the spraying was stopped and 13 pounds of charcoal powder (Norit SG, American Norit Company, Jacksonville, Florida) was added at three equidistant locations on the top of the mixer, while the mixer was running. Two minutes were allowed for the sand to tack with carbon powder, and return to a free flowing state, then spraying was resumed and the process repeated spraying the remaining 3.5 gallons of technical protein colloid-Altosid slurry. When the sand again began to drag, a second 13 pounds of charcoal powder were added, and the mixture blended for another 2 minutes. To dry remaining dampness from the granule surfaces, 13 pounds of (Eagle Picher MN-47 Diatomite) drying agent was added and the mixer operated for a final 2 minutes. The granule manufacturing was now complete, the free flowing granule was then augured from the ribbon blender into a bagging tower, until bagged for use.

Small ¾ cubic yard rotary mixers have been used to make 200 pound experimental batches with an average batch time of 15 minutes. Conventional ribbon blender mixing equipment has been used to produce 4,000 pounds of this product with an average batch time, including the time required to charge and unload the mixer, of 20 minutes.

EXAMPLE II

Into a 15 gallon stainless steel tank with heating jacket adjusted to maintain 130° F., was placed 8.3 gallons of 130' water. A high speed sheer mixer, such as used in paint manufacturing, was inserted into the water and adjusted to 800 to 1,000 rpm. Next, 3 pounds of technical urea was dissolved in the hot water to retard crosslinking, which begins with the later addition of Glyoxal, until the urea gases off thus preventing the fluid viscosity from increasing while spraying. Next, 13.5 pounds of dry powdered collagen protein (Technical Protein Colloid # 1 V, Swift Adhesives and Coatings, Chicago, Illinois) was slowly added into the vortex of the water and mixed for 3 minutes to dissolve the powder. The high speed blade was then removed and a slow speed paddle blade inserted and adjusted from about 30 to 50 rpm. Two minutes before beginning to spray, 300 ml of Glyoxal (General Dynamics Corporation, South Plainfield, New Jersey) was added and mixed thoroughly with the protein colloid solution.

Then a ribbon blender of 3 cubic yard capacity was charged with 950 pounds of washed # 30 Red Flint Filter Sand (American Materials, Eau Claire, Wisconsin). While mixing at low speed in a pressure vessel with heating jacket, the vessel was pressured with air to 40 psi. The ribbon blender was started and the Glyoxal treated protein colloid solution sprayed through a flat fan nozzle system (Spraying Systems # 8001 nozzles) affixed inside the ribbon blender, and adjusted to spray onto the rotating sand. When the sand changed from free flowing to the point at which it began to drag after the spraying of approximately 2.8 gallons, and before it began clumping, the spraying was stopped and 13.6 pounds of Altosid mosquito control pesticide, isopropyl-(2E,4E)-11-methoxy-3,7,11-trimethyl2,4-dodecadenoate (Zoecon Industries, Dallas, Texas) Prem Powder was added at three equidistant locations on the top of the mixer, while the mixer was running. Two minutes were allowed for the sand to tack on Premix powder, and return to a free flowing state, then spraying was resumed and the process repeated spraying a second 2.8 gallons of technical protein colloid. When the sand again began to drag, an additional 13.6 pounds of Altosid Premix powder were added, and the mixture blended for another 2 minutes to attach the Premix powder onto the granules. Then spraying was resumed a third time and a third 2.8 gallons of technical protein colloid applied, followed by the final addition of 13.6 pounds of Premix powder after which the mixer was allowed to blend for a third 2 minutes to attach the final layer of Premix powder. To dry remaining dampness from the granule surfaces, 10 pounds of Diatomite MN-47 drying agent (Eagle Picher, Cincinnati, Ohio) was added and the mixer operated for a final 2 minutes. The granule manufacture was now complete, and the free flowing granule augured from the ribbon blender into a bagging tower, until bagged.

Small ¾ cubic yard rotary mixers have been used to make 200 pound experimental batches with an average batch time of 20 minutes. Conventional ribbon blender mixing equipment has been used to produce 4,000 pounds of this product with an average batch time, including the time required to change and unload the mixer, of 30 minutes.

Field Efficacy Trials

Field trials were conducted with an Altosid 20 Day Controlled Release Sand Granule in Wright County, Minnesota, using sod lined wading pools placed in full sunlight and treated at an equivalent rate of 5 lbs. of granules per acre. Early instar *Aedes vexans* larvae were introduced into each pool on 5 to 7 day intervals to permit weekly pupal collections to be made to assess the duration of control provided by each granule treatment.

At the end of the first 36 days, the pools had overflowed several times due to heavy rainfall, and the control level had diminished. A decision was made to repeat the applications a second time, making the treatment and awaiting to make the first larval introduction at two weeks post treatment. The second trials were concluded 28 days post treatment due to cool rainy weather.

Table 1 shows a summary of trials with various Altosid 5 Day Prehatch Controlled Release Granule formulations applied to field mosquito breeding sites.

TABLE 1

| Example Formulation | Lb. A.I. Per Day | Date Treated | Pupa Coll. | Percent Mortality |
|---|---|---|---|---|
| I | 0.0043 | 5/14 | 5/22 | 99 |
| II | 0.0042 | 6/10 | 6/27 | 100 |
| I | 0.0035 | 6/12 | 6/19 | 90 |
| I | 0.0035 | 6/12 | 6/26 | 98 |
| I | 0.0035 | 6/12 | 6/28 | 100 |

Table 2 shows a summary of field trials conducted with an Altosid 20 Day Prehatch Controlled Release Granule Example II (0.0028 lb. A.I./day) conducted in wading pools in Wright County, Minnesota.

TABLE 2

| Pool | Rate | Number Dead Pupa | Number Dead Adult | Number Live Adult | Number Mort. |
|---|---|---|---|---|---|
| Series I | | | | | |
| Elapsed Time After Application: 3 Days | | | | | |
| A | 5.0 | 80 | 13 | 0 | 100 |
| B | 5.0 | 22 | 5 | 0 | 100 |
| C | 5.0 | 4 | 5 | 86 | 10 |
| Ref. | 0.0 | 2 | 1 | 89 | 3 |
| Elapsed Time After Application: 10 Days | | | | | |
| A | 5.0 | 59 | 14 | 5 | 94 |
| B | 5.0 | 100 | 0 | 0 | 100 |
| C | 5.0 | 100 | 0 | 0 | 100 |
| Ref. | 0.0 | 2 | 2 | 44 | 8 |
| Elapsed Time After Application: 23 Days | | | | | |
| A | 5.0 | 45 | 6 | 27 | 65 |
| B | 5.0 | 115 | 2 | 3 | 98 |
| C | 5.0 | 110 | 1 | 0 | 100 |
| Ref. | 0.0 | 15 | 11 | 27 | 49 |
| Elapsed Time After Application: 30 Days | | | | | |
| A | 5.0 | 0 | 0 | 12 | 0 |
| B | 5.0 | 17 | 33 | 49 | 51 |
| C | 5.0 | 25 | 15 | 61 | 40 |
| Ref. | 0.0 | 0 | 0 | 30 | 0 |
| Series II | | | | | |
| Elapsed Time After Application: 19 Days | | | | | |
| A | 5.0 | 204 | 0 | 0 | 100 |
| B | 5.0 | 62 | 0 | 0 | 100 |
| C | 7.5 | 112 | 0 | 0 | 100 |
| Elapsed Time After Application: 28 Days | | | | | |
| A | 5.0 | 178 | 17 | 0 | 100 |
| B | 5.0 | 140 | 68 | 8 | 96 |
| C | 7.5 | 55 | 18 | 0 | 100 |

Table 3 shows a summary of field trials with an Altosid 20 day prehatch controlled release granule conducted in field mosquito breeding sites in Wright County, Minnesota.

TABLE 3

| Example Formulation | Lb. A.I. Per Day | Date Treated | Pupa Coll. | Percent Mortality |
|---|---|---|---|---|
| II | 0.0028 | 6/6 | 6/27 | 99 |
| II | 0.0042 | 6/6 | 6/26 | 100 |
| II | 0.0028 | 6/24 | 6/27 | 100 |
| II | 0.0028 | 6/20 | 6/25 | 100 |

An examination of Tables 1, 2 and 3 clearly shows the effectiveness of the pest control means in obtaining 100% mortality of *Aedes vexans* mosquito populations in most instances during the temperate season, at very low dosage rates of active ingredient (A.I.). Given a rate of 5 pounds of the pest control means applied to waters containing mosquito larvae under field conditions, the invention protects the highly UV sensitive pesticide, Altosid, from sunlight and regulates its slow release over the desired time period at concentrations which result in mosquito control.

EXAMPLE III

Fluid bed dryers, granulators and coaters such as the Glatt Powder Coater Granulator allow the formulation of pest control means having a first active region on the surface and a second active ingredient incorporated as the core. When an active ingredient having a high hydrophilicity, hydroscopic and soluble character is used as the core of the granule, it is of great importance that the core be coated uniformly. A uniform coating around an active core ensures that premature release of the active due to a thin or irregular area in the coating will not occur. Each granule particle is uniformly coated with technical protein colloid of the correct molecular weight and/or crosslinking to properly regulate the desired release of active ingredient. This allows the manufacture of very uniformly coated granule particles and, in turn, prevents premature release of the core active ingredient.

Into a ten gallon stainless steel tank, with heating jacket adjusted to maintain the temperature at 130° F., is placed 2 gallons of 130° F. water. A high speed sheer mixer, such as used in paint manufacturing, is inserted into the water and adjusted to 800–1000 rpm. Next 7.7 pounds of dry powdered collagen protein (Technical Protein Colloid # 1-V, Swift Adhesives and Coatings, Chicago, Illinois) is slowly added to the vortex of the water and mixed for two minutes to dissolve the powder. The high speed blade is then removed and a slow speed paddle is inserted and adjusted to run at 30–50 rpm. Then five gallons of S-Ethyl-N, N, dipropylthiocarbonate plus N,N-dialkyl-1, 1-dichloroacetamide (Eradicane commercially available from Stauffer Chemical Company of Westport, Connecticut). 6.7 pounds/gallon emulsifiable concentrate herbicide is added and mixed while the fluid mixture is heated to a temperature of 120° F.

While the technical protein colloid and pesticide slurry is heating, a fluid bed dryer (Glatt Air Techniques, Inc.) is prepared for operation. The Glatt Powder Coater Granulator (GPCG) is a twin chamber unit having one chamber for the coating of particles and a second chamber into which the particles are transferred for storage.

The GPCG is then charged with prilled urea 46-0-0 solid fertilizer (Farmland Industries, Inc., Kansas City, Missouri). The fluid bed of the GPCG is then activated, and the urea particles are subjected to air pressure and lifted above the bed of the GPCG by air pressure infused from the bottom of the machine. The technical protein colloid is then sprayed on the particles through openings in the GPCG chamber. Once the technical protein colloid is completely applied to the urea particles and allowed to dry, another coating of technical protein colloid-Eradicane slurry is applied to the particulate composition. When the protein is completely applied and the urea particles have completed drying, the granule manufacturing is now complete. The GPCG is deactivated and depressurized and the coated urea granules are removed from the application chamber.

EXAMPLE IV

The processes and devices of Example III are used in the production of a fertilizer composition containing urea. The protein colloid is crosslinked and processed as in Example III, however, an active ingredient is not included within the proteinatious slurry. While the technical protein colloid is heating a fluid bed dryer (Glatt Air Techniques, Inc.) is prepared for operation. The Glatt powder coated grandulator (GPCG) is a twin chamber unit having one chamber for the coating of particles in a second into which the particles are transferred for storage.

The GPCG is then charged with urea prills, liquid particles of urea fertilizer (commercially available from Farmland Industries, Inc., Kansas City, Missouri). The fluid bed of the GPCG is then activated, and the urea particles are subjected to air pressure and lifted above the bed of the GPCG by air pressure infused from the bottom of the machine. The technical protein colloid is then sprayed on the particles through openings in the GPCG chamber. Once the technical protein colloid is completely applied to the urea prills and allowed to dry, another coating of technical protein colloid is applied. When the protein is completely applied and the urea prill particles have dried, the granule manufacture is now complete. GPCG is deactivated and depressurized and the formed granuli are removed from the application chamber.

The above discussion and Examples provides a basis for understanding and practicing the invention. However, since many embodiments of the invention can be made without departing from the spirit and scope of the invention, the invention resides solely in the claims hereinafter appended.

I claim:

1. A controlled, slow release pest control composition, comprising a pesticide, a core covered by at least one layer of a solid, proteinatious composition, said proteinaceous composition comprising about 5–30 wt-% of the pest control composition, and a drying layer comprising a sorbative dust; wherein the rate of dissolution of the proteinaceous layer causes a timed release of the pesticide into the environment.

2. The composition of claim 1 wherein the pesticide is dispersed in the proteinatious layer.

3. The composition of claim 1 wherein the pest control composition comprises more than one proteinaceous layer with a spacing layer between the proteinaceous layers, the pesticide being dispersed in the spacing layer wherein the spacing layer comprises a particulate material selected from the group consisting of active carbon, diatomaceous earth, a silicate, a pesticide, or mixtures thereof.

4. The composition of claim 1 wherein the proteinatious composition is crosslinked.

5. The composition of claim 4 wherein the proteinatious layer is crosslinked with a dialdehyde.

6. The composition of claim 4 wherein the proteinatious layer is crosslinked with a trivalent metal ion.

7. The composition of claim 1 wherein the pesticide comprises a mosquito control agent.

8. The composition of claim 7 wherein the mosquito control agent comprises isopropyl-(2E,4E)-11-methoxy-2,7,11-trimethyl-2,4-dodecadiene.

9. The composition of claim 1 wherein the pesticide is selected from the group consisting of trichloroacetic acid, 2,4-dichlorophenoxyacetic acid, and 4-amino-6-tertiary butyl-3-(methythio)-AS-triazina-5-(4HN)-one.

10. The composition or claim 1 wherein the molecular weight of the proteinatious material ranges from 10,000 to 120,000.

11. The composition of claim 1 wherein the molecular weight of the proteinatious material ranges from 20,000 to 80,000.

12. The composition of claim 4 wherein the crosslinking agent is added at a level of 0.1 to 2 wt-% based on the proteinatious material.

13. The composition of claim 1 wherein the pest control agent is present in the total composition in an amount of about 3 to 16 wt-%.

14. The composition of claim 1 wherein the proteinatious material is present in the total composition in an amount of about 0.5 to 4.5 wt-%.

15. The composition of claim 7 wherein the spacing layer is present in the total composition in an amount of about 1 to 6 wt-%.

16. The composition of claim 1 wherein said core is inert.

17. The composition of claim 16 wherein said inert core is selected from the group consisting of sand, vermiculite, diatomaceous earth, clay, and particulate cellulose.

18. The composition of claim 1 wherein said core comprises a solid.

19. The composition of claim 18 wherein said solid core comprises an active ingredient selected from the group consisting of pesticide, insecticide, fertilizer, and herbicide.

20. The composition of claim 1 wherein said core comprises a porous particle carrying an active ingredient.

21. The composition of claim 20 wherein said active ingredient is selected from the group consisting of pesticide, insecticide, fertilizer, and herbicide.

22. A controlled, slow release pest control composition, comprising a pesticide, a core covered by at least two layers of a solid, proteinaceous composition, a spacing layer, said proteinaceous layers separated by said spacing layer, wherein the proteinaceous layers comprise about 5-30 wt-% of the pest control layers and the rate of dissolution of the proteinaceous layer causes a timed release of the pesticide into the environment.

23. The composition of claim 22 wherein the pesticide is dispersed in the proteinatious layer.

24. The composition of claim 22 wherein the pesticide is dispersed into the spacing layer.

25. The composition of claim 22 wherein the proteinatious composition is crosslinked.

26. The composition of claim 25 wherein the proteinatious layer is crosslinked with a dialdehyde.

27. The composition of claim 25 wherein the proteinatious layer is crosslinked with a trivalent metal ion.

28. The composition of claim 22 wherein the spacing layer is selected from the group consisting of carbon, diatomaceous earth, and activated silica.

29. The composition of claim 22 wherein the pesticide comprises a mosquito control agent.

30. The composition of claim 29 wherein the mosquito control agent comprises isopropyl-(2E,4E)-11-methoxy-2,7,11-trimethyl-2,4-dodecadiene.

31. The composition of claim 22 wherein the pesticide is selected from the group consisting of trichloroacetic acid, 2,4-dichlorophenoxyacetic acid, and 4-amino-6-tertiary butyl-3-(methythio)-AS-triazina-5-(4HN)-one.

32. The composition of claim 22 wherein the molecular weight of the proteinatious material ranges from 10,000 to 120,000.

33. The composition of claim 22 wherein the molecular weight of the proteinatious material ranges from 20,000 to 80,000.

34. The composition of claim 25 wherein the crosslinking agent is added at a level of 0.1 to 2 wt-% based on the proteinatious material.

35. The composition of claim 22 wherein the pest control agent is present in the total composition in an amount of about 3 to 16 wt-%.

36. The composition of claim 22 wherein the proteinatious material is present in the total composition in an amount of about 0.5 to 4.5 wt-%.

37. The composition of claim 28 wherein the spacing layer is present in the total composition in an amount of about 1 to 6 wt-%.

38. The composition of claim 22 having an outer covering layer comprising a drying agent.

39. The composition of claim 22 wherein said core is inert.

40. The composition of claim 39 wherein said inert core is selected from the group consisting of sand, vermiculite, diatomaceous earth, clay, and particulate cellulose.

41. The composition of claim 22 wherein said core comprises a solid.

42. The composition of claim 41 wherein said solid core comprises an active ingredient selected from the group consisting of pesticide, insecticide, fertilizer, and herbicide.

43. The composition of claim 22 wherein said core comprises a porous particle carrying an active ingredient.

44. The composition of claim 43 wherein said active ingredient is selected from the group consisting of pesticide, insecticide, fertilizer, and herbicide.

45. A controlled, slow release pest control composition comprising a pesticide, buoyant particles, said pesticide being vacuum loaded onto said buoyant particles, a core covered by at least two layers of solid, proteinaceous composition, a spacing layer, said proteinaceous layers separated by said spacing layer, wherein the proteinaceous layers comprise about 5-30 wt-% of the pest control composition and the rate of dissolution of the proteinaceous layer causes a time release dispersion of the pesticide-ladden buoyant particles into the environment.

46. The composition of claim 45 wherein the pesticide-laden buoyant particles are dispersed into the spacing layer.

47. The composition of claim 45 wherein the pesticide-laden buoyant particles are dispersed into the proteinatious layer.

48. The composition of claim 46 wherein the pesticide is additionally dispersed into the proteinatious layers.

49. The composition of claim 47 wherein pesticide is additionally dispersed into the spacing layer.

50. The composition of claim 45 wherein the proteinatious composition is crosslinked.

51. The composition of claim 45 wherein the proteinatious layer is crosslinked with a dialdehyde.

52. The composition of claim 51 wherein the proteinatious layer is crosslinked with a trivalent metal ion.

53. The composition of claim 45 wherein the spacing layer is selected from the group comprising carbon, diatomaceous earth, and activated silica.

54. The composition of claim 45 wherein the pesticide comprises a mosquito control agent.

55. The composition of claim 54 wherein the mosquito control agent comprises isopropyl-(2E,4E)-11-methoxy-2,7,11-trimethyl-2,4-dodecadiene.

56. The composition of claim 45 wherein the pesticide is selected from the group consisting of trichloroacetic acid, 2,4-dichlorophenoxyacetic acid, and 4-amino-6-tertiary butyl-3-(methythio)-AS-triazina-5-(4HN)-one.

57. The composition of claim 45 wherein the molecular weight of the proteinatious material ranges from 10,000 to 120,000.

58. The composition of claim 45 wherein the molecular weight of the proteinatious material ranges from 20,000 to 80,000.

59. The composition of claim 50 wherein the cross-linking agent is added at a level of 0.1 to 2 wt-% based on the proteinatious material.

60. The composition of claim 45 wherein the pest control agent is present in the total composition in an amount of about 3 to 16 wt-%.

61. The composition of claim 45 wherein the proteinatious material is present in the total composition in an amount of about 0.5 to 4.5 wt-%.

62. The composition of claim 53 wherein the spacing layer is present in the total composition in an amount of about 1 to 6 wt-%.

63. The composition of claim 45 having an outer covering layer comprising a drying agent.

64. The composition of claim 45 wherein said core is inert.

65. The composition of claim 64 wherein said core is selected from the group consisting of sand, vermiculite, diatomaceous earth, clay, and particulate cellulose.

66. The composition of claim 45 wherein said core comprises a solid.

67. The composition of claim 61 wherein said solid core comprises an active ingredient selected from the group consisting of pesticide, insecticide, fertilizer, and herbicide.

68. The composition of claim 45 wherein said core comprises a porous particle carrying an active ingredient.

69. The composition of claim 68 wherein said active ingredient is selected from the group consisting of pesticide, insecticide, fertilizer, and herbicide.

* * * * *